United States Patent [19]

Winchell

[11] Patent Number: 4,474,016
[45] Date of Patent: Oct. 2, 1984

[54] STERILE COOLING SYSTEM

[75] Inventor: David A. Winchell, Spring Grove, Ill.

[73] Assignee: Baxter Travenol Laboratories, Inc., Deerfield, Ill.

[21] Appl. No.: 471,994

[22] Filed: Mar. 4, 1983

[51] Int. Cl.³ .............................................. B65B 63/08
[52] U.S. Cl. ...................................... 62/60; 62/78;
62/371; 62/457; 62/530; 206/484; 229/43;
435/1; 435/283
[58] Field of Search .................. 62/530, 529, 371, 457,
62/60, 306, 78; 229/43; 206/484; 435/1, 283

[56] References Cited

U.S. PATENT DOCUMENTS

| | | | |
|---|---|---|---|
| 2,006,706 | 7/1935 | Barnes et al. | 62/530 |
| 2,662,520 | 12/1953 | McMahon | 435/1 |
| 2,807,402 | 9/1957 | Nelbach | 62/371 |
| 3,406,531 | 10/1968 | Swenson et al. | 62/78 |
| 3,496,731 | 2/1970 | Longo | 62/371 |

OTHER PUBLICATIONS

"Slush Technique in Renal Surgery", Peirce, et al, *AORN Journal* Feb. 1977, vol. 25, No. 2, pp. 223-226.
*AORN Journal,* Nov. 1977, vol. 26, No. 5, p. 989.
*AORN Journal,* May 1977, vol. 25, No. 6, pp. 1044 and 1045.

*Primary Examiner*—Ronald C. Capossela
*Attorney, Agent, or Firm*—John P. Kirby, Jr.; Bradford R. L. Price; George H. Gerstman

[57] ABSTRACT

A cooling system is provided for organs during transplant surgery. A disposable receptacle (10) has a sterilizable interior and is formed of a material that is sufficiently rigid to maintain its shape normally without collapsing but sufficiently flexible to be squeezable manually. A disposable flexible container (16) is located inside the receptacle. The flexible container (16) contains a liquid solution that is adapted to be chilled in a freezer. The flexible container (16) and its contents are sterilizable and useful for providing cooling for organs during surgical transplants. The disposable receptacle (10) has a peelable lid (14) that is sealed to a tray portion (12) to enable the sterilizable container (16) to be aseptically removed from the receptacle (10).

16 Claims, 6 Drawing Figures

4,474,016

STERILE COOLING SYSTEM

TECHNICAL FIELD

This invention concerns a novel cooling system for organs, and more particularly, a system using disposable elements for cooling organs during surgery.

BACKGROUND ART

It is known in the art to use an iced saline slush for cooling organs during surgery. As used herein, the term "organ" is intended to refer to any animal body element that is cooled during surgery.

In one known cooling system, the slush is prepared one day prior to surgery. Two sterile plastic bags are introduced into a sterile surgical canister. The plastic bags are filled with sterile saline solution, are fastened with sterile rubber bands, capped and tape-sealed. The canister is placed in a freezer overnight. Subsequently, during surgery, the sterile plastic bags are removed from the canister by a scrub nurse and are placed on a basin on a sterile table. The iced saline within the bags is broken up with a mallet in order to provide the consistency of slush desired. The slush is then placed adjacent the organ as desired by the surgeon.

In another known cooling technique, bottles of slush solution, which have been precooled in a referigerator, are placed in a freezer in order for the solution to become supercooled. The bottles are removed from the freezer, allowed to stand at room temperature for several minutes, uncapped and the contents are poured into a sterile stainless steel bowl provided by a scrub nurse. The supercooled solution becomes slush as it hits the bowl, and the slush is used for cooling purposes.

It can be seen that in certain prior art slush techniques, the provision of sterile frozen slush in the operating room is relatively complicated. It is, therefore, an object of the present invention to provide a low cost, convenient way to provide frozen slush to the operating room.

It is another object of the present invention to provide a cooling system for organs using a disposable receptacle and container and enabling the delivery of sterile slush in an efficient and relatively inexpensive manner.

Other objects and advantages of the invention will become apparent as the description proceeds.

DISCLOSURE OF THE INVENTION

In accordance with the present invention, a cooling system for organs is provided. The cooling system comprises a disposable receptacle having a sterilizable interior. The receptacle is formed of a material that is sufficiently rigid to maintain its shape normally without collapsing but is sufficiently flexible to be squeezable manually. In this manner, the person squeezing the receptacle can generally determine the condition of the receptacle's contents.

The system further comprises a disposable flexible container located inside the receptacle. The flexible container contains a liquid solution that is adapted to be chilled in a freezer. The flexible container and its contents are sterilizable and are useful for providing cooling for organs during surgery. The disposable receptacle includes means for enabling the sterilizable container to be aseptically removed from the receptacle when sterile and to remain in sterile condition.

In the illustrative embodiment, the receptacle comprises a tray portion with the enabling means comprising a cover that is manually removable from the tray portion. The tray portion comprises a bottom with two contiguous sides and two contiguous ends extending upwardly therefrom, with the cover comprising peelable lid. The flexible container comprises a bag formed of flexible plastic material and the liquid solution comprises a saline solution.

In the illustrative embodiment, the system of the present invention comprises the steps of providing a closed disposable receptacle having therein a closed disposable flexible container that contains a liquid solution. The disposable receptacle and the disposable flexible container are sterilized while the container is within the closed receptacle. The combined receptacle and container are cooled in a freezer and the cooled receptacle and container are thereafter removed from the freezer. The cooled container is aseptically removed from the receptacle for using the cooled liquid as a cooling medium during surgery. After use of the receptacle and container, they are disposed of.

A more detailed explanation of the invention is provided in the following description and claims, and is illustrated in the accompanying drawings.

DETAILED DESCRIPTION OF THE ILLUSTRATIVE EMBODIMENT

Figure 1:
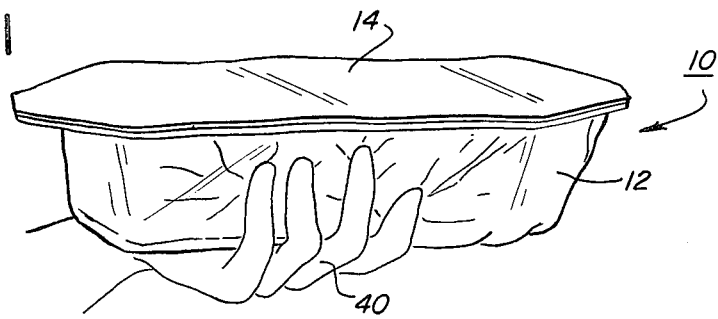
FIG. 1 is a perspective view of a cooling system constructed in accordance with the principles of the present invention, with the cover of the receptacle intact.
Figure 2:
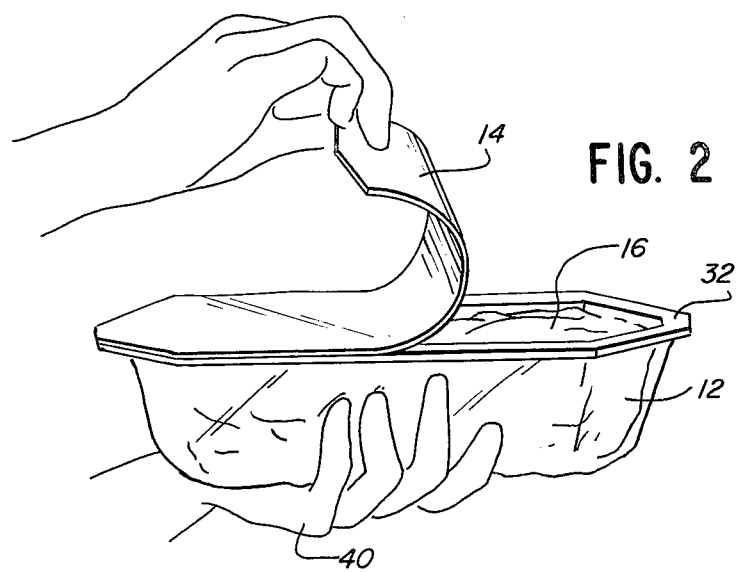
FIG. 2 is a perspective view thereof, showing the cover being removed.
Figure 3:
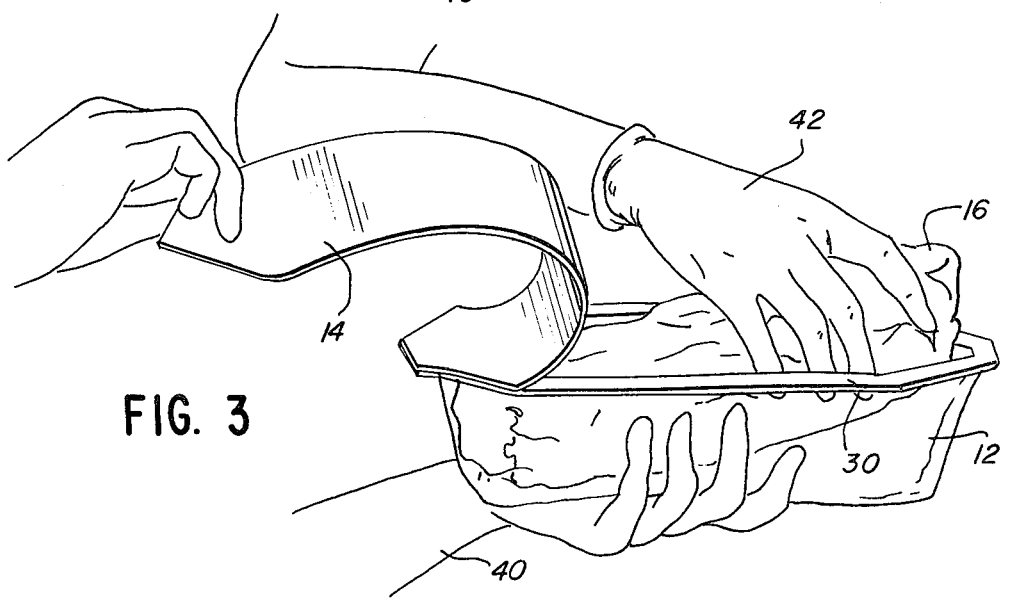
FIG. 3 is a perspective view thereof, showing the cover being removed and also showing the disposable flexible container being aseptically removed from the receptacle.

Referring to FIGS. 1–3, a cooling system is shown therein comprising a disposable receptacle 10. Receptacle 10 includes a tray portion 12 and means 14 for enabling a disposable flexible container 16, that is located within the receptacle 10, to be removed aseptically from receptacle 10.

Tray portion 12 is formed of a material that is sufficiently rigid to maintain its shape normally without collapsing but sufficiently flexible to be squeezable manually. As an example, although no limitation is intended, tray portion 12 could comprise a plastic material such as TPX ® plastic (poly (4-methyl-1-pentene)) or PETG (polyethylene terephthalate G) having a thickness between 0.01 inch and 0.015 inch. As illustrated most clearly in FIG. 1, a person squeezing the receptacle will find it sufficiently flexible to be able to determine a condition of the receptacle's contents. In the illustrative embodiment, flexible container 16 contains a saline solution that is adapted to be chilled in a freezer. The flexible container and the saline solution are sterilizable and are useful for providing cooling for organs during surgery. By squeezing tray portion 12 as illustrated in FIG. 1, the nurse can determine the slush consistency of the liquid solution within container 16, i.e., the extent to which the solution is frozen.

Figure 4:
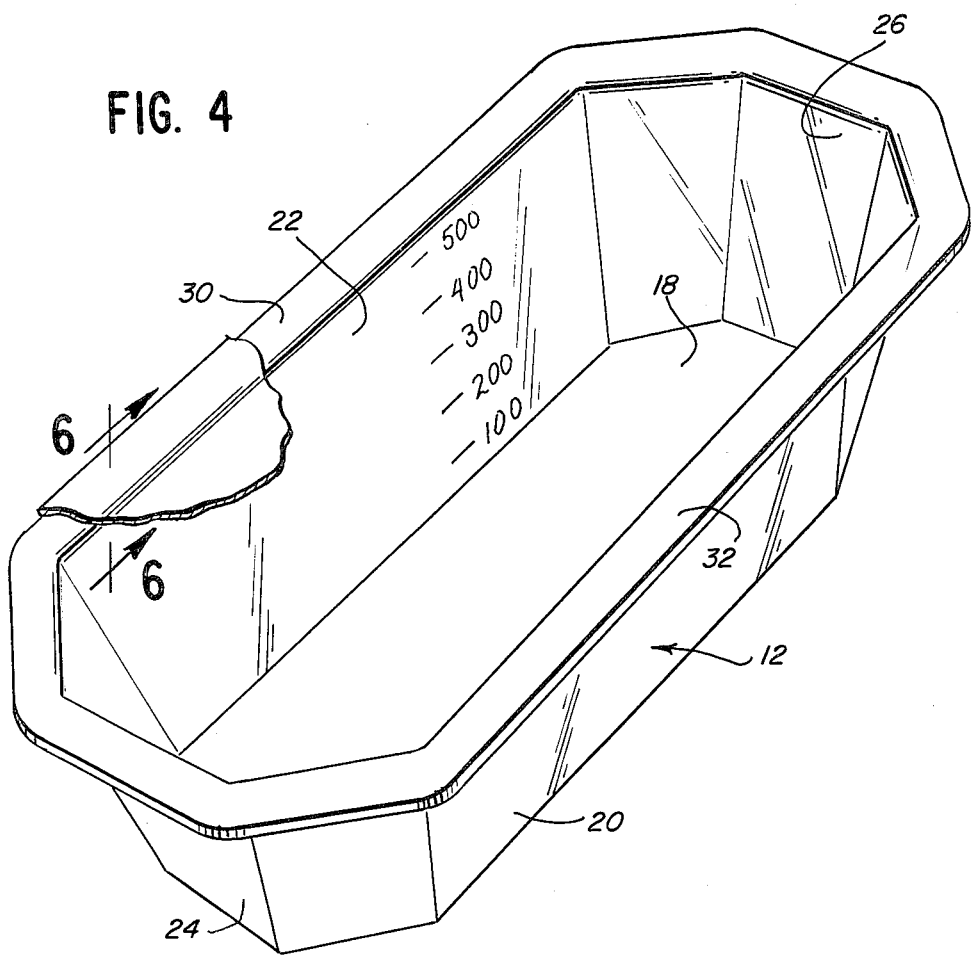
FIG. 4 is a perspective view of the tray portion of the cooling system of FIG. 1.
Figure 6:
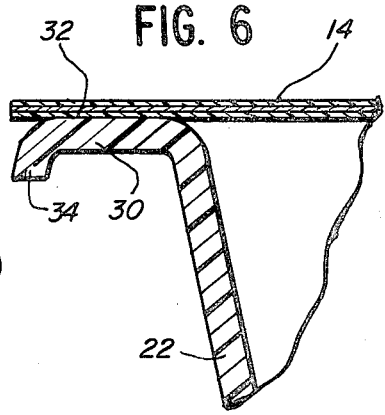
FIG. 6 is a broken, enlarged cross-sectional view, taken along the plane of the line 6—6 of FIG. 4.

The details of construction of the disposable receptacle can be more readily seen by referring to FIGS. 4 and 6. As illustrated in FIG. 6, tray portion 12 comprises a bottom 18 with two contiguous sides 20, 22 extending upwardly therefrom and also two contiguous ends 24 and 26 from a top peripheral lip 30 which has a horizontal top surface 32 and its distal end comprises an edge 34. The means 14 for enabling the sterilizable container 16 to be removed aseptically from the receptacle 10 comprises a peelable lid as illustrated in FIG. 6 preferably formed of a flexible material that is sealed to horizontal surface 32 of the tray portion 12. Although no limitation is intended, peelable lid 14 could comprise an aluminum foil having a plastic (for example, TPX ® plastic) laminated on the underside of the foil and heat sealed to horizontal surface 32. Lid 14 preferably has a plastic, for example, MYLAR ® plastic, laminated on the top side of the aluminum foil with the total lid laminate 14 preferably having a thickness of not more than 0.005 inch.

Figure 5:
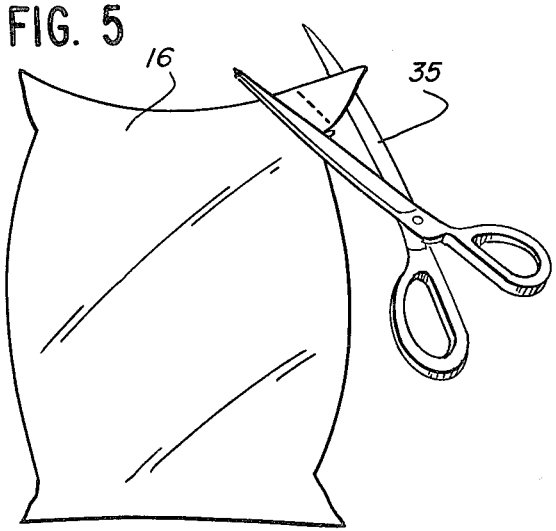
FIG. 5 is a diagrammatic view of a flexible container containing the cooling solution, for use with the tray of FIG. 4, and also showing a means for opening the disposable flexible container.

Referring to FIG. 5, flexible container 16 is shown therein and comprises a bag formed of a flexible plastic material and containing a liquid saline solution. Although no limitation is intended, bag 16 is preferably formed of a flexible plastic material such as PVC (polyvinyl chloride) or PE (polyethylene) having a thickness of between 0.010 inch and 0.015 inch. The solution contained within bag 16 may be any solution that is desirably used as slush in surgical cooling systems. As a specific example, although no limitation is intended, the solution within bag 16 may be 0.9 percent sodium chloride, lactated Ringer's solution and PLASMA-LYTE A ® solution. The bag 16 may be capable of holding approximately one liter of solution and tray portion 12 should be capable of containing bag 16 with the solution therein. It is preferred that disposable receptacle 10 have a volume slightly greater than the volume of the bag 16.

A surgical scissors 35 may be provided with bag 16 and contained within tray portion 12 with bag 16. Alternatively, another surgical cutting means may be used for opening bag 16 if desired, with the surgical cutting means being located on a sterile table in the operating room.

Referring back to FIGS. 1-3, the system of cooling comprises the provision of closed disposable receptacle 10 having therein closed disposable flexible container 16 containing the saline solution. This is illustrated in FIG. 1. Disposable receptacle 10 with its disposable flexible container 16 therein are preferably sterilized together, for example, by steam sterilization. Alternatively, the receptacle 10 and container 16 could be sterilized separately and thereafter aseptically combined by introducing the sterile container 16 into the sterile receptacle 10.

Once the sterilization is accomplished, the combination receptacle 10 with container 16 is placed in a freezer to cool the solution within container 16 a desired amount. After sufficient cooling, the combination disposable receptacle 10 with container 16 is placed in a freezer to cool the solution within container 16 a desired amount. After sufficient cooling, the combination disposable receptacle 10 with disposable container 16, in a sterilized condition, is removed from the freezer. In this condition the liquid contents of container 16 have been cooled, the contents of container 16 are sterile, container 16 is sterile and the interior of receptacle 10 is sterile. Tray portion 12 may be squeezed on the outside as illustrated in FIG. 1 in order to determine the consistency of the contents of container 16. Although hand 40 (FIG. 1) may not be sterile, the interior of receptacle 10 and the contents therein are sterile.

As illustrated in FIG. 2, lid 14 may be peeled off with a hand that is unclean, so long as there is no contact with the interior of tray portion 12 and container 16. Container 16 may then be aseptically removed from tray portion 12, as illustrated in FIG. 3, by a "clean" hand 42. Bag 16 containing the slush can then be used in the manner desired by the surgeon, to cool the patient's organ. The tray portion 12, lid portion 14 and container 16 are then discarded after use.

Different surgeons require differnt consistencies of the liquid within container 16. For example, while some surgeons do not want the solution within container 16 to become frozen to any extent, other surgeons use a solution that comprises ice chips. Further, while some surgeons do not allow the solution to come into contact with the organ to be cooled, other surgeons place the cooled solution in intimate contact with the organ. In any event, container 16 must be sterile because either container 16 or the solution within container 16 is placed either near the organ or in intimate contact therewith.

In using the cooling system of the present invention, the nurse is advised to inspect the disposable receptacle 10 and not to use the disposable receptacle 10 if any portion thereof is ruptured or cracked. It is also preferred that disposable receptacle 10 and its contents be stored in a suitable freezer at $-8°$ C. (17.6° F.) for a minimum of four hours prior to use. The slush consistency is then checked by squeezing the tray and lid 14 is peeled off so that container 16 may be aseptically removed with forceps or a gloved hand. If the surgeon wants to remove the slush from container 16, a sterile cutting means must be used to slit the bag at one end and the slush is emptied into the sterile field.

It is seen that a novel cooling system for organs has been provided, which is relatively inexpensive and convenient, and enables the user to dispose of the system after it is used. Although an illustrative embodiment of the invention has been shown and described, it is to be understood that various modifications may be made by those skilled in the art without departing from the spirit and scope of the present invention.

That which is claimed is:

1. A cooling system for organs, which comprises: a disposable receptacle having a sterilizable interior and formed of a material that is sufficiently rigid to maintain its shape normally without collapsing but sufficiently flexible to be squeezable manually whereby the person squeezing the receptacle can generally determine a condition of the receptacle's contents;

a disposable flexible container located inside the receptacle, said flexible container containing a liquid solution that is adapted to be chilled in a freezer, said flexible container and its contents being sterilizable and useful for providing cooling for organs during surgery;

said disposable receptacle including means for enabling said sterilizable container to be aseptically removed from said receptacle when sterile and remain in sterile condition; and a tray portion with said enabling means comprising a cover that is manually removable from said tray portion.

2. A cooling system as described in claim 1, said tray portion comprising a bottom with two contiguous sides and two contiguous ends extending upwardly therefrom, said cover comprising a peelable lid.

3. A cooling system as described in claim 2, said tray portion formed of a plastic material and said peelable lid formed of a flexible material that is sealed to said tray portion.

4. A cooling system as described in claim 3, said flexible container comprising a bag formed of a flexible plastic material with said liquid solution comprising saline solution; said receptacle having a volume that is slightly greater than the volume of the flexible container.

5. A cooling system as described in claim 2, said sides and ends forming a top lip with said peelable lid being sealed to said top lip.

6. A cooling system as described in claim 1, said flexible container comprising a bag formed of a flexible plastic material.

7. A cooling system as described in claim 1, said liquid solution comprising saline solution.

8. a cooling system as described in claim 1, said receptacle having a volume that is slightly greater than the volume of the flexible container.

9. A system for cooling organs comprising the steps of:
providing a closed disposable receptacle having a sterilizable interior and formed of a material that is sufficiently rigid to maintain its shape normally without collapsing but sufficiently flexible to be squeezable manually whereby the person squeezing the receptacle can generally determine a condition of the receptacle's contents, said receptacle having therein a closed disposable flexible container that contains a liquid solution;
sterilizing the disposable receptacle and the disposable flexible container while the container is within the closed receptacle;
cooling the combined receptacle and container in a freezer;
thereafter removing the cooled receptacle and container from the freezer;
aseptically removing the cooled container from the receptacle for using the cooled liquid as a cooling medium during surgery; and
disposing of the receptacle and container after use thereof.

10. A system for cooling organs as described in claim 9, including the step of after aseptically removing the cooled container from the receptacle, aseptically opening the container to remove the cooled liquid therefrom.

11. A system for cooling organs as described in claim 9, including the step of using the cooled container with the cooled liquid therein as the cooling medium during surgery.

12. A system for cooling organs as described in claim 9, wherein the closed disposable receptacle has a removable lid; and the step of after removing the cooled receptacle from the freezer, removing the lid to provide access to the sterile cooled container therein.

13. A system for cooling organs comprising the steps of:
providing a closed disposable receptacle having therein a closed disposable flexible container that contains a liquid solution;
sterilizing the disposable receptacle;
sterilizing the disposable flexible container;
aseptically introducing the sterile disposable flexible container into the disposable receptacle;
cooling the combined receptacle and container in a freezer;
thereafter removing the cooled receptacle and container from the freezer;
aseptically removing the cooled container from the receptacle for using the cooled liquid as a cooling medium during surgery; and
disposing of the receptacle and container after use thereof.

14. A system for cooling organs as described in claim 13, including the step of after aseptically removing the cooled container from the receptacle, aseptically opening the container to remove the cooled liquid therefrom.

15. A system for cooling organs as described in claim 13, including the step of using the cooled container with the cooled liquid therein as the cooling medium during surgery.

16. A system for cooling organs as described in claim 13, wherein the closed disposable receptacle has a removable lid; and the step of after removing the cooled receptacle from the freezer, removing the lid to provide access to the sterile cooled container therein.

* * * * *